(12) United States Patent
Beers et al.

(10) Patent No.: US 7,476,672 B2
(45) Date of Patent: Jan. 13, 2009

(54) ACETYLENIC COMPOUNDS USEFUL IN TREATING INFLAMMATORY DISORDERS

(75) Inventors: Scott Beers, Flemington, NJ (US);
Elizabeth A. Malloy, Easton, PA (US);
Michael P. Wachter, Bloomsbury, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 548 days.

(21) Appl. No.: 11/328,929

(22) Filed: Jan. 10, 2006

(65) Prior Publication Data
US 2006/0111352 A1    May 25, 2006

Related U.S. Application Data

(62) Division of application No. 10/626,155, filed on Jul. 24, 2003, now Pat. No. 7,022,703.

(60) Provisional application No. 60/356,697, filed on Jul. 24, 2002.

(51) Int. Cl.
*A61K 31/5375* (2006.01)
*C07D 265/30* (2006.01)

(52) U.S. Cl. .................. 514/237.8; 544/106; 544/162; 546/184; 548/566; 564/305; 514/231.2

(58) Field of Classification Search ............... 544/106, 544/162; 546/184; 548/566; 564/305; 514/231.2, 514/237.8
See application file for complete search history.

(56) References Cited

U.S. PATENT DOCUMENTS

| | | | | | |
|---|---|---|---|---|---|
| 4,652,584 | A | * | 3/1987 | Carson | 514/524 |
| 4,742,084 | A | * | 5/1988 | Carson | 514/654 |
| 6,239,077 | B1 | * | 5/2001 | Andoh et al. | 504/312 |
| 7,022,703 | B2 | * | 4/2006 | Beers et al. | 514/237.8 |

* cited by examiner

*Primary Examiner*—Golam M Shameem
(74) *Attorney, Agent, or Firm*—Thomas Dodd

(57) ABSTRACT

This invention is directed to acetylenic compounds as inhibitors of a nicotinamide adenine dinucleotide oxidase hydride donor useful in treating or ameliorating a reactive oxygen species mediated inflammatory disorder.

2 Claims, No Drawings

ACETYLENIC COMPOUNDS USEFUL IN TREATING INFLAMMATORY DISORDERS

CROSS-REFERENCE TO RELATED APPLICATIONS

This application is a divisional of U.S. application Ser. No. 10/626,155, filed on Jul. 24, 2003 now U.S. Pat. No. 7,022,703. The present invention also claims the benefit of earlier filed U.S. provisional patent application, Ser. No. 60/356,697, filed on Jul. 24, 2002.

STATEMENT REGARDING FEDERALLY SPONSORED RESEARCH OR DEVELOPMENT

The research and development of the invention described below was not federally sponsored.

BACKGROUND OF THE INVENTION

This invention relates to a series of acetylenic compounds, pharmaceutical compositions and methods for use thereof. More particularly, the acetylenic compounds of the present invention are nicotinamide adenine dinucleotide oxidase hydride donor inhibitors useful in treating or ameliorating inflammatory disorders.

The nicotinamide adenine dinucleotides (NAD, NADH, NADP and NADPH) are essential cofactors in all living systems and function as hydride acceptors (NAD, NADP) and hydride donors (NADH, NADPH) in biochemical redox reactions. The six-step biosynthetic pathway begins with the oxidation of aspartate to iminosuccinic acid, which is then condensed with dihydroxyacetone phosphate to give quinolinic acid. Phosphoribosylation and decarboxylation of quinolinic acid gives nicotinic acid mononucleotide. Adenylation of this mononucleotide followed by amide formation completes the biosynthesis of NAD. An additional phosphorylation gives NADP (Begley, T. P., et al., The Biosynthesis of Nicotinamide Adenine Dinucleotides in Bacteria, *Vitam. Horm.*, 2001, 61, 103-119).

The importance of reactive oxygen species (ROS) in the pathogenesis of inflammatory diseases is increasingly recognized. During inflammation, polymorphonuclear leucocytes (PMN) and macrophages become stimulated by lipopolysaccharide (LPS) and tumor necrosis factor alpha (TNF-α) as well as cytokines IFN-γ and interleukin-2 (IL-2). Stimulation results in the cellular assembly of a nicotinamide adenine dinucleotide oxidase hydride donor, in particular NADPH, a membrane bound enzyme which is the major source of ROS. The generation of ROS has been shown to be elevated up to 10 fold in patients with various inflammatory and autoimmune rheumatic diseases (R. Miesel, et al., Suppression of Inflammatory Arthritis by Simultaneous Inhibition of Nitric Oxide Synthase and NADPH Oxidase, *Free Radical Biology & Medicine*, 1996, 20(3), 75-81).

Two known inhibitors of NADPH Oxidase, diphenylene iodoniumchloride (DPI) and staurosporine have been shown to have antiinflammatory effects in mice with potassium peroxochromate arthritis. Daily doses of 2.8 μmol/kg of DPI and 30 nmol/kg staurosporine inhibited the arthritis by 50%. Complete inhibition was obtained with 10 mmol/kg DPI while 85% inhibition of the arthritis was achieved with 100 nmol staurosporine (R. Miesel, et al., Antiinflammatory Effects of NADPH Oxidase Inhibitors, *Inflammation*, 1995, 19(3), 347-362).

The antirheumatic drug Piroxicam has been shown to reduce levels of ROS in human patients with rheumatoid arthritis and osteoarthritis by 25% at pharmacological doses. In vitro studies showed that this inhibition was caused by interference of the activation of NADPH Oxidase (P. Biemond, et al., Superoxide Production by Polymorphonuclear Leucocytes in Rheumatoid Arthritis and Osteoarthritis: In vivo Inhibition by the Antirheumatic Drug Piroxicam Due to the Interference With the Activation of the NADPH Oxidase, *Annals of the Rheumatic Diseases*, 1986, 45, 249-255).

The deposition of β-amyloid in the brain is the key pathogenic event in Alzheimer's disease. Recently, β-amyloid has been shown to induce the stimulation of NADPH oxidase in human neutrophils and microglia in a dose dependent manner. The subsequent production of ROS is at least in part responsible for the neurodegenerative effects of β-amyloid (V. D. Bianca, et al., β-Amyloid Activates the $O_2$-Forming NADPH Oxidase in Microglia, Monocytes, and Neutrophils, *The Journal of Biological Chemistry*, 1999, 274, 15493-15499).

Thus, there is a need for the acetylenic compounds of the present invention as nicotinamide adenine dinucleotide oxidase hydride donor inhibitors and a method for use of such compounds in treating or ameliorating a reactive oxygen species mediated inflammatory disorder.

SUMMARY OF THE INVENTION

The present invention relates to acetylenic compounds of Formula (I):

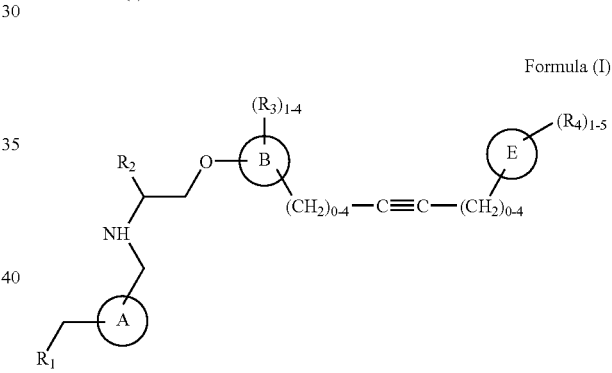

Formula (I)

wherein:

A is $(C_{5-6})$cycloalkyldiyl, cyclic heteroalkyldiyl, aryldiyl or heteroaryldiyl;

B is aryldiyl or heteroaryldiyl;

E is aryidiyl or heteroaryidiyl;

$R_1$ is $(C_{3-8})$cycloalkyl-$(R_8)_q$, cyclic heteroalkyl-$(R_9)_q$, aryl-$(R_8)_q$, heteroaryl-$(R_9)_q$ or $NR_5R_6$;

$R_5$ is hydrogen, $(C_{1-12})$alkanyl-$R_7$, C(O)H, C(O)—$(C_{1-12})$alkanyl-$R_7$, $CO_2H$, C(O)O—$(C_{1-12})$alkanyl-$R_7$, $(C_{3-8})$cycloalkyl-$(R_8)_q$, cyclic heteroalkyl-$(R_9)_q$, aryl-$(R_8)_q$ or heteroaryl-$(R_9)_q$; wherein cyclic heteroalkyl-$(R_9)_q$ and heteroaryl-$(R_9)_q$ are attached to the nitrogen atom of $NR_5R_6$ via a ring carbon atom;

$R_6$ is hydrogen or $(C_{1-8})$alkanyl-$R_7$;

$R_7$ is hydrogen, $(C_{1-8})$alkoxy-$(R_{10})_s$, C(O)H, C(O)—$(C_{1-8})$alkanyl-$(R_{10})_s$, C(O)—$R_a$, $CO_2H$, C(O)O—$(C_{1-8})$alkanyl-$(R_{10})_s$, C(O)O—$R_a$, OC(O)—$(C_{1-8})$alkanyl-$(R_{10})_s$, OC(O)—$R_a$, $NH_2$, $NH(C_{1-8}$alkanyl-$(R_{10})_s)$, $N(C_{1-8}$alkanyl-$(R_{10})_s)_2$, cyano, $(halo)_{1-3}$, hydroxy or $R_a$;

$R_a$ is $(C_{3-8})$cycloalkyl-$(R_{11})_q$, cyclic heteroalkyl-$(R_{12})_q$, aryl-$(R_{11})_q$ or heteroaryl-$(R_{12})_q$;

$(R_8)_q$ is hydrogen, $(C_{1-8})$alkanyl-$(R_{10})_s$, $(C_{1-8})$alkoxy-$(R_{10})_s$, C(O)H, C(O)—$(C_{1-8})$alkanyl-$(R_{10})_s$, CO$_2$H, C(O)O—$(C_{1-8})$alkanyl-$(R_{10})_s$, NH$_2$, NH($C_{1-8}$alkanyl-$(R_{10})_s$), N($C_{1-8}$alkanyl-$(R_{10})_s)_2$ or halogen;

$(R_9)_q$ is hydrogen, $(C_{1-8})$alkanyl-$(R_{10})_s$, C(O)H, C(O)—$(C_{1-8})$alkanyl-$(R_{10})_s$, CO$_2$H or C(O)O—$(C_{1-8})$alkanyl-$(R_{10})_s$ when attached to a nitrogen atom; wherein $(R_9)_q$ is hydrogen, $(C_{1-8})$alkanyl-$(R_{10})_s$, $(C_{1-8})$alkoxy-$(R_{10})_s$, C(O)H, C(O)—$(C_{1-8})$alkanyl-$(R_{10})_s$, CO$_2$H, C(O)O—$(C_{1-8})$alkanyl-$(R_{10})_s$, NH$_2$, NH($C_{1-8}$alkanyl-$(R_{10})_s$), N($C_{1-8}$alkanyl-$(R_{10})_s)_2$ or halogen when attached to a carbon atom;

$(R_{10})_s$ is hydrogen, $(C_{1-8})$alkoxy, NH$_2$, NH($C_{1-8}$alkanyl), N($C_{1-8}$alkanyl)$_2$, (halo)$_{1-3}$ or hydroxy;

$(R_{11})_q$ is hydrogen, $(C_{1-8})$alkanyl, $(C_{1-8})$alkoxy, NH$_2$, NH($C_{1-8}$alkanyl), N($C_{1-8}$alkanyl)$_2$ or halogen;

$(R_{12})_q$ is hydrogen or $(C_{1-8})$alkanyl;

$R_2$ is hydrogen, $(C_{1-8})$alkanyl-$R_7$, $(C_{1-8})$alkoxy-$R_7$, C(O)H, C(O)—$(C_{1-8})$alkanyl-$R_7$, CO$_2$H, C(O)O—$(C_{1-8})$alkanyl-$R_7$, NH$_2$, NH($C_{1-8}$alkanyl-$R_7$), N($C_{1-8}$alkanyl-$R_7$)$_2$, cyano, halogen, hydroxy or $R_a$;

$R_3$ and $R_4$ are independently hydrogen, $(C_{1-8})$alkanyl-$R_7$, C(O)H, C(O)—$(C_{1-8})$alkanyl-$R_7$, CO$_2$H, C(O)O—$(C_{1-8})$alkanyl-$R_7$, $(C_{3-8})$cycloalkyl-$(R_8)_q$ or aryl-$(R_8)_q$ when attached to a nitrogen atom; wherein $R_3$ and $R_4$ are independently hydrogen, $(C_{1-8})$alkanyl-$R_7$, $(C_{1-8})$alkoxy-$R_7$, C(O)H, C(O)—$(C_{1-8})$alkanyl-$R_7$, CO$_2$H, C(O)O—$(C_{1-8})$alkanyl-$R_7$, NH$_2$, NH($C_{1-8}$alkanyl-$R_7$), N($C_{1-8}$alkanyl-$R_7$)$_2$, cyano, halogen, hydroxy, $(C_{3-8})$cycloalkyl-$(R_8)_q$, cyclic heteroalkyl-$(R_9)_q$, aryl-$(R_8)_q$ or heteroaryl-$(R_9)_q$ when attached to a carbon atom;

q is 1, 2, 3, 4 or 5; and, s is 1 or 2;

and enantiomers, diastereomers, tautomers, solvates and pharmaceutically acceptable salts thereof.

An aspect of the present invention includes a method for treating or ameliorating a reactive oxygen species mediated inflammatory disorder in a subject in need thereof comprising administering to the subject a therapeutically effective amount of a compound selected from Formula (I).

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

"Alkyl" refers to a saturated or unsaturated, branched, straight-chain or cyclic monovalent hydrocarbon radical derived by the removal of one hydrogen atom from a single carbon atom of a parent alkane, alkene or alkyne, thus forming the point of attachment for the radical. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl, cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred aspects, the alkyl groups are ($C_{1-8}$) alkyl, with ($C_{1-4}$) alkyl being particularly preferred. Where a cyclic alkyl is specifically intended, the terms "cycloalkyl", "cycloalkanyl", "cycloalkenyl" and "cycloalkynyl" are used consistent with the definitions of alkanyl, alkenyl and alkynyl. In preferred aspects, the cycloalkyl groups are monocyclic alkyls of from 3-8 carbon atoms or fused bicycloalkyls of from 9 to 10 carbon atoms. Examples of preferred cycloalkyls include, and are not limited to, cyclopropyl, cyclobutyl, cyclopentyl, cyclohexyl or cycloheptyl.

"Alkanyl" refers to a saturated branched, straight-chain or cyclic monovalent hydrocarbon radical derived by the removal of one hydrogen atom from a single carbon atom of the parent alkane, thus forming the point of attachment for the radical. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred aspects, the alkanyl groups are ($C_{1-8}$) alkanyl, with ($C_{1-4}$) being particularly preferred.

"Alkenyl:" refers to an unsaturated branched, straight-chain or cyclic monovalent hydrocarbon radical having at least one carbon-carbon double bond and derived by the removal of one hydrogen atom from a single carbon atom of the parent alkene, thus forming the point of attachment for the radical. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is ($C_{2-8}$) alkenyl, with ($C_{2-4}$) being particularly preferred.

"Alkyldiyl" refers to a saturated or unsaturated, branched, straight-chain or cyclic divalent hydrocarbon radical derived by the removal of one hydrogen atom from each of two different carbon atoms of the parent alkane, alkene or alkyne, or by the removal of two hydrogen atoms from a single carbon atom of the parent alkane, alkene or alkyne, thus forming the points of attachment for the radical as a linking group or the point of attachment for the radical as a spiro moiety, respectively. The two monovalent radical centers can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyidiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl, cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methylprop-2-en-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used consistent with the definitions of alkanyl, alkenyl and alkynyl. In preferred aspects, the alkyldiyl group is ($C_{1-8}$) alkyldiyl, with ($C_{1-4}$) being particularly preferred. Also preferred are saturated acyclic alkyldiyl radicals in which the radical centers are at the terminal carbons, e.g., methandiyl; ethan-1,2-diyl; propan-1,3-diyl; butan-1,4-diyl; and the like (also referred to as alkylenos, as previously defined).

"Cyclic Heteroalkyl" refers to a saturated or unsaturated cyclic alkyl radical in which one or more carbon atoms are independently replaced with the same or different heteroatom. Typical heteroatoms to replace the carbon atom(s) include, but are not limited to, N, P, O, S, Si, etc. Where a specific level of saturation is intended, the nomenclature "cyclic heteroalkanyl" or cyclic heteroalkenyl; etc." is used. Typical cyclic heteroalkyl moieties include, but are not limited to, radicals derived from epoxides, imidazolidine, morpholine, piperazine, piperidine, pyrazolidine, pyrrolidine, quinuclidine and the like. In preferred aspects, the cyclic heteroalkyl is a 3-6 membered cyclic heteroalkyl. Particularly preferred cyclic heteroalkyls are saturated or partially unsaturated five membered monocyclic heteroalkyls of which at least one member is a N, O or S atom and which optionally contain one additional O atom or one additional N atom; saturated or partially unsaturated six membered monocyclic heteroalkyls of which one, two or three members are a N atom, wherein at most two nitrogen atoms are adjacent; or, saturated or partially unsaturated nine or ten membered bicyclic heteroalkyls of which at least one member is a N, O or S atom and which optionally contains one, two or three additional N atoms, wherein at most two nitrogen atoms are adjacent. Examples of particularly preferred cyclic heteroalkyls include, and are not limited to, 2-pyrrolinyl, 3-pyrrolinyl, pyrrolidinyl, 1,3-dioxolanyl, 2-imidazolinyl, imidazolidinyl, 2-pyrazolinyl, pyrazolidinyl, piperidinyl, morpholinyl or piperazinyl.

"Parent Aromatic Ring System" refers to an unsaturated cyclic or polycyclic ring system having a conjugated Π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like "Aryl" refers to a monovalent aromatic hydrocarbon radical derived by the removal of one hydrogen atom from a single carbon atom of the parent aromatic ring system, thus forming the point of attachment for the radical. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In preferred aspects, the aryl group is derived from a parent aromatic monocyclic ring system containing 6 carbon atoms (as in phenyl), a parent aromatic fused bicyclic ring system containing 10 carbon atoms (as in naphthyl) or a parent aromatic fused tricyclic ring system containing 14 hydrogen carbon atoms (as in anthracenyl).

"Aryldiyl" refers to a divalent unsaturated hydrocarbon radical derived by the removal of one hydrogen atom from each of two different carbon atoms of the parent aromatic ring system, thus forming the point of attachment for the radical as a linking group; or, to a divalent partially unsaturated hydrocarbon radical derived by the removal of two hydrogen atoms from a single carbon atom of the parent aromatic ring system, thus forming the point of attachment for the radical as a spiro moiety. The two monovalent radical centers can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms are each independently replaced with a heteroatom. Typical heteratoms to replace the carbon atoms include, but are not limited to, N, P, O, S, Si etc. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Heteroaryl" refers to a monovalent heteroaromatic radical derived by the removal of one hydrogen atom from a single atom of the parent heteroaromatic ring system, thus forming the point of attachment for the radical. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like. Preferred heteroaryls are derived from: parent heteroaromatic monocyclic ring systems containing five members of which at least one member is a N, O or S atom and which optionally contains one, two or three additional N atoms; parent heteroaromatic monocyclic ring systems having six members of which one, two or three members are an N atom; parent heteroaromatic fused bicyclic ring systems having nine members of which at least one member is a N, O or S atom and which optionally contain one, two or three additional N atoms; parent heteroaromatic fuse bicyclic ring systems having ten members of which one, two or three members are a N atom; or, parent heteroaromatic fused tricyclic ring systems containing 13 or 14 members of which at least one member is a N, O or S atom and which optionally contain one, two or three additional N atoms. Examples of preferred heteroaryls include, and are not limited to, furyl, thienyl, pyrrolyl, oxazolyl, thiazolyl, imidazolyl, pyrazolyl, isoxazolyl, isothiazolyl, thiadiazolyl, tetrazolyl, pyrimidinyl, pyrazinyl and triazinyl.

"Heteroaryldiyl" refers to a divalent heteroaromatic radical derived by the removal of one hydrogen atom from each of two different atoms of a parent heteroaromatic ring system or by the removal of two hydrogen atoms from a single atom of the parent heteroaromatic ring system, thus forming the point of attachment for the radical as a linking group, wherein the two monovalent radical centers can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like. In preferred aspects, the heteroaryldiyl group is a 5-20 membered heteroaryldiyl, with a 5-10 membered heteroaryldiyl being particularly preferred.

"Alkoxy" refers to an —OR substituent where R is alkyl, wherein alkyl is as previously defined. "Hydroxy" refers to an —OR substituent where R is hydrogen.

"Independently" means that when a group is substituted with more than one substituent that the substituents may be the same or different. The term "dependently" means that the substituents are specified in an indicated combination of structure variables.

The present invention relates to acetylenic compounds of Formula (I):

Formula (I)

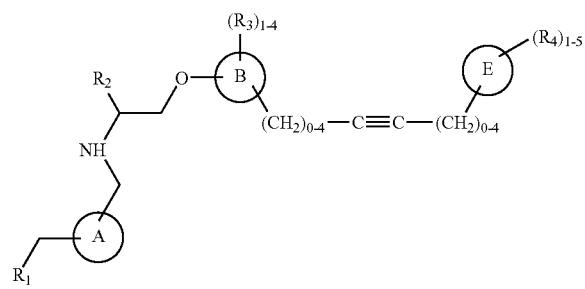

wherein:
A is $(C_{5-6})$cycloalkyldiyl, cyclic heteroalkyldiyl, aryldiyl or heteroaryldiyl;
B is aryldiyl or heteroaryldiyl;
E is aryldiyl or heteroaryldiyl;
$R_1$ is $(C_{3-8})$cycloalkyl-$(R_8)_q$, cyclic heteroalkyl-$(R_9)_q$, aryl-$(R_8)_q$, heteroaryl-$(R_9)_q$ or $NR_5R_6$;
$R_5$ is hydrogen, $(C_{1-12})$alkanyl-$R_7$, C(O)H, C(O)—$(C_{1-12})$alkanyl-$R_7$, $CO_2H$, C(O)O—$(C_{1-12})$alkanyl-$R_7$, $(C_{3-8})$cycloalkyl-$(R_8)_q$, cyclic heteroalkyl-$(R_9)_q$, aryl-$(R_8)_q$ or heteroaryl-$(R_9)_q$; wherein cyclic heteroalkyl-$(R_9)_q$ and heteroaryl-$(R_9)_q$ are attached to the nitrogen atom of $NR_5R_6$ via a ring carbon atom;
$R_6$ is hydrogen or $(C_{1-8})$alkanyl-$R_7$;
$R_7$ is hydrogen, $(C_{1-8})$alkoxy-$(R_{10})_s$, C(O)H, C(O)—$(C_{1-8})$alkanyl-$(R_{10})_s$, C(O)—$R_a$, $CO_2H$, C(O)O—$(C_{1-8})$alkanyl-$(R_{10})_s$, C(O)O—$R_a$, OC(O)—$(C_{1-8})$alkanyl-$(R_{10})_s$, OC(O)—$R_a$, $NH_2$, $NH(C_{1-8}$alkanyl-$(R_{10})_s)$, $N(C_{1-8}$alkanyl-$(R_{10})_s)_2$, cyano, (halo)$_{1-3}$, hydroxy or $R_a$;
$R_a$ is $(C_{3-8})$cycloalkyl-$(R_{11})_q$, cyclic heteroalkyl-$(R_{12})_q$, aryl-$(R_{11})_q$ or heteroaryl-$(R_{12})_q$;
$(R_8)_q$ is hydrogen, $(C_{1-8})$alkanyl-$(R_{10})_s$, $(C_{1-8})$alkoxy-$(R_{10})_s$, C(O)H, C(O)—$(C_{1-8})$alkanyl-$(R_{10})_s$, $CO_2H$, C(O)O—$(C_{1-8})$alkanyl-$(R_{10})_s$, $NH_2$, $NH(C_{1-8}$alkanyl-$(R_{10})_s)$, $N(C_{1-8}$alkanyl-$(R_{10})_s)_2$ or halogen;
$(R_9)_q$ is hydrogen, $(C_{1-8})$alkanyl-$(R_{10})_s$, C(O)H, C(O)—$(C_{1-8})$alkanyl-$(R_{10})_s$, $CO_2H$ or C(O)O—$(C_{1-8})$alkanyl-$(R_{10})_s$ when attached to a nitrogen atom; wherein $(R_9)_q$ is hydrogen, $(C_{1-8})$alkanyl-$(R_{10})_s$, $(C_{1-8})$alkoxy-$(R_{10})_s$, C(O)H, C(O)—$(C_{1-8})$alkanyl-$(R_{10})_s$, $CO_2H$, C(O)O—$(C_{1-8})$alkanyl-$(R_{10})_s$, $NH_2$, $NH(C_{1-8}$alkanyl-$(R_{10})_s)$, $N(C_{1-8}$alkanyl-$(R_{10})_s)_2$ or halogen when attached to a carbon atom;
$(R_{10})_s$ is hydrogen, $(C_{1-8})$alkoxy, $NH_2$, $NH(C_{1-8}$alkanyl), $N(C_{1-8}$alkanyl)$_2$, (halo)$_{1-3}$ or hydroxy;
$(R_{11})_q$ is hydrogen, $(C_{1-8})$alkanyl, $(C_{1-8})$alkoxy, $NH_2$, $NH(C_{1-8}$alkanyl), $N(C_{1-8}$alkanyl)$_2$ or halogen;
$(R_{12})_q$ is hydrogen or $(C_{1-8})$alkanyl;
$R_2$ is hydrogen, $(C_{1-8})$alkanyl-$R_7$, $(C_{1-8})$alkoxy-$R_7$, C(O)H, C(O)—$(C_{1-8})$alkanyl-$R_7$, $CO_2H$, C(O)O—$(C_{1-8})$alkanyl-$R_7$, $NH_2$, $NH(C_{1-8}$alkanyl-$R_7)$, $N(C_{1-8}$alkanyl-$R_7)_2$, cyano, halogen, hydroxy or $R_a$;
$R_3$ and $R_4$ are independently hydrogen, $(C_{1-8})$alkanyl-$R_7$, C(O)H, C(O)—$(C_{1-8})$alkanyl-$R_7$, $CO_2H$, C(O)O—$(C_{1-8})$alkanyl-$R_7$, $(C_{3-8})$cycloalkyl-$(R_8)_q$ or aryl-$(R_8)_q$ when attached to a nitrogen atom; wherein $R_3$ and $R_4$ are independently hydrogen, $(C_{1-8})$alkanyl-$R_7$, $(C_{1-8})$alkoxy-$R_7$, C(O)H, C(O)—$(C_{1-8})$alkanyl-$R_7$, $CO_2H$, C(O)O—$(C_{1-8})$alkanyl-$R_7$, $NH_2$, $NH(C_{1-8}$alkanyl-$R_7)$, $N(C_{1-8}$alkanyl-$R_7)_2$, cyano, halogen, hydroxy, $(C_{3-8})$cycloalkyl-$(R_8)_q$, cyclic heteroalkyl-$(R_9)_q$, aryl-$(R_8)_q$ or heteroaryl-$(R_9)_q$ when attached to a carbon atom;
q is 1, 2, 3, 4 or 5; and,
s is 1 or 2;

and enantiomers, diastereomers, tautomers, solvates and pharmaceutically acceptable salts thereof.

Aspects of the present invention also include compounds of Formula (I) wherein A is aryldiyl.

Another aspect of the present invention includes compounds of Formula (I) wherein A is benzenediyl.

Aspects of the present invention include compounds of Formula (I) wherein B is aryldiyl.

Another aspect of the present invention includes compounds of Formula (I) wherein B is benzenediyl.

Aspects of the present invention include compounds of Formula (I) wherein E is aryldiyl.

Another aspect of the present invention includes compounds of Formula (I) wherein E is benzenediyl.

Aspects of the present invention include compounds of Formula (I) wherein $R_1$ is $(C_{5-8})$cycloalkyl-$(R_8)_q$, cyclic heteroalkyl-$(R_9)_q$, aryl-$(R_8)_q$, heteroaryl-$(R_9)_q$ or $NR_5R_6$.

Another aspect of the present invention includes compounds of Formula (I) wherein $R_1$ is $NR_5R_6$.

Aspects of the present invention include compounds of Formula (I) wherein $R_5$ is hydrogen, $(C_{1-10})$alkanyl-$R_7$, C(O)H, C(O)—$(C_{1-4})$alkanyl-$R_7$, $CO_2H$, C(O)O—$(C_{1-4})$alkanyl-$R_7$, $(C_{3-6})$cycloalkyl-$(R_8)_q$, cyclic heteroalkyl-$(R_9)_q$, aryl-$(R_8)_q$ or heteroaryl-$(R_9)_q$; wherein cyclic heteroalkyl-$(R_9)_q$ and heteroaryl-$(R_9)_q$ are attached to the nitrogen atom of $NR_5R_6$ via a ring carbon atom.

Another aspect of the present invention includes compounds of Formula (I) wherein $R_5$ is hydrogen, $(C_{1-10})$alkanyl-$R_7$ or aryl-$(R_8)_q$.

A further aspect of the present invention includes compounds of Formula (I) wherein $R_5$ is hydrogen, $(C_{1-10})$alkanyl-$R_7$ or phenyl-$(R_8)_q$.

Aspects of the present invention include compounds of Formula (I) wherein $R_6$ is hydrogen or $(C_{1-4})$alkanyl-$R_7$.

Aspects of the present invention include compounds of Formula (I) wherein $R_7$ is hydrogen, $(C_{1-4})$alkoxy-$(R_{10})_s$, C(O)H, C(O)—$(C_{1-4})$alkanyl-$(R_{10})_s$, C(O)—$R_a$, $CO_2H$, C(O)O—$(C_{1-4})$alkanyl-$(R_{10})_s$, C(O)O—$R_a$, OC(O)—$(C_{1-4})$alkanyl-$(R_{10})_s$, OC(O)—$R_a$, $NH_2$, NH($C_{1-4}$alkanyl-$(R_{10})_s$), N($C_{1-4}$alkanyl-$(R_{10})_s)_2$, cyano, (halo)$_{1-3}$, hydroxy or $R_a$.

Another aspect of the present invention includes compounds of Formula (I) wherein $R_7$ is hydrogen, OC(O)—$R_a$, $NH_2$, NH($C_{1-4}$alkanyl-$(R_{10})_s$), N($C_{1-4}$alkanyl-$(R_{10})_s)_2$ or $R_a$.

A further aspect of the present invention includes compounds of Formula (I) wherein $R_7$ is hydrogen, OC(O)—$R_a$, N($C_{1-4}$alkanyl-$(R_{10})_s)_2$ or $R_a$.

Aspects of the present invention include compounds of Formula (I) wherein $R_a$ is $(C_{3-6})$cycloalkyl-$(R_{11})_q$, cyclic heteroalkyl-$(R_{12})_q$, aryl-$(R_{11})_q$ or heteroaryl-$(R_{12})_q$.

Another aspect of the present invention includes compounds of Formula (I) wherein $R_a$ is cyclic heteroalkyl-$(R_{12})_q$ or aryl-$(R_{12})_q$.

A further aspect of the present invention includes compounds of Formula (I) wherein $R_a$ is pyrrolidinyl-$(R_{12})_q$, piperidinyl-$(R_{12})_q$, morpholinyl-$(R_{12})_q$ or phenyl-$(R_{11})_q$.

Aspects of the present invention include compounds of Formula (I) wherein $(R_8)_q$ is hydrogen, $(C_{1-4})$alkanyl-$(R_{10})_s$, $(C_{1-4})$alkoxy-$(R_{10})_s$, C(O)H, C(O)—$(C_{1-4})$alkanyl-$(R_{10})_s$, $CO_2H$, C(O)O—$(C_{1-4})$alkanyl-$(R_{10})_s$, $NH_2$, NH($C_{1-4}$alkanyl-$(R_{10})_s$), N($C_{1-4}$alkanyl-$(R_{10})S)_2$ or halogen.

Another aspect of the present invention includes compounds of Formula (I) wherein $(R_8)_q$ is hydrogen.

Aspects of the present invention include compounds of Formula (I) wherein $(R_9)_q$ is hydrogen, $(C_{1-4})$alkanyl-$(R_{10})_s$, C(O)H, C(O)—$(C_{1-4})$alkanyl-$(R_{10})_s$, $CO_2H$ or C(O)O—$(C_{1-4})$alkanyl-$(R_{10})_s$ when attached to a nitrogen atom; wherein $(R_9)_q$ is hydrogen, $(C_{1-4})$alkanyl-$(R_{10})_s$, $(C_{1-4})$alkoxy-$(R_{10})_s$, C(O)H, C(O)—$(C_{1-4})$alkanyl-$(R_{10})_s$, $CO_2H$, C(O)O—$(C_{1-4})$alkanyl-$(R_{10})_s$, $NH_2$, NH($C_{1-4}$alkanyl-$(R_{10})_s$), N($C_{1-4}$alkanyl-$(R_{10})_s)_2$ or halogen when attached to a carbon atom.

Another aspect of the present invention includes compounds of Formula (I) wherein $(R_9)_q$ is hydrogen.

Aspects of the present invention include compounds of Formula (I) wherein $(R_{10})_s$ is hydrogen, $C_{1-4}$alkoxy, $NH_2$, NH($C_{1-4}$alkanyl), N($C_{1-4}$alkanyl)$_2$, (halo)$_{1-3}$ or hydroxy.

Another aspect of the present invention includes compounds of Formula (I) wherein $(R_{10})_s$ is hydrogen.

Aspects of the present invention include compounds of Formula (I) wherein $(R_{11})_q$ is hydrogen, $(C_{1-4})$alkanyl, $(C_{1-4})$alkoxy, $NH_2$, NH($C_{1-4}$alkanyl), N($C_{1-4}$alkanyl)$_2$ or halogen.

Another aspect of the present invention includes compounds of Formula (I) wherein $(R_{11})_q$ is hydrogen.

Aspects of the present invention include compounds of Formula (I) wherein $(R_{12})_q$ is hydrogen or $(C_{1-4})$alkanyl.

Aspects of the present invention include compounds of Formula (I) wherein $R_2$ is hydrogen, $(C_{1-4})$alkanyl-$R_7$, $(C_{1-4})$alkoxy-$R_7$, C(O)H, C(O)—$(C_{1-4})$alkanyl-$R_7$, $CO_2H$, C(O)O—$(C_{1-4})$alkanyl-$R_7$, $NH_2$, NH($C_{1-4}$alkanyl-$R_7$), N($C_{1-4}$alkanyl-$R_7)_2$, cyano, halogen, hydroxy or $R_a$.

Another aspect of the present invention includes compounds of Formula (I) wherein $R_2$ is hydrogen or $(C_{1-4})$alkanyl-$R_7$.

Aspects of the present invention include compounds of Formula (I) wherein $R_3$ and $R_4$ are independently hydrogen, $(C_{1-4})$alkanyl-$R_7$, C(O)H, C(O)—$(C_{1-4})$alkanyl-$R_7$, $CO_2H$, C(O)O—$(C_{1-4})$alkanyl-$R_7$, $(C_{3-6})$cycloalkyl-$(R_8)_q$ or aryl-$(R_8)_q$ when attached to a nitrogen atom; wherein $R_3$ and $R_4$ are independently hydrogen, $(C_{1-4})$alkanyl-$R_7$, $(C_{1-4})$alkoxy-$R_7$, C(O)H, C(O)—$(C_{1-4})$alkanyl-$R_7$, $CO_2H$, C(O)O—$(C_{1-4})$alkanyl-$R_7$, $NH_2$, NH($C_{1-4}$alkanyl-$R_7$), N($C_{1-4}$alkanyl-$R_7)_2$, cyano, halogen, hydroxy, $(C_{3-6})$cycloalkyl-$(R)_q$, cyclic heteroalkyl-$(R_9)_q$, aryl-$(R_8)_q$ or heteroaryl-$(R_9)_q$ when attached to a carbon atom.

Another aspect of the present invention includes compounds of Formula (I) wherein $R_3$ and $R_4$ are hydrogen when attached to a nitrogen atom; wherein $R_3$ and $R_4$ are independently hydrogen, $(C_{1-4})$alkanyl-$R_7$ or halogen when attached to a carbon atom.

A further aspect of the present invention includes compounds of Formula (I) wherein $R_3$ and $R_4$ are independently hydrogen, $(C_{1-4})$alkanyl-$R_7$ or halogen.

A further aspect of the present invention includes compounds of Formula (I) wherein $R_3$ and $R_4$ are independently hydrogen, $(C_{1-4})$alkanyl-$R_7$, chlorine or fluorine.

Aspects of the present invention include compounds of Formula (I) wherein q is 1.

Aspects of the present invention include compounds of Formula (I) wherein s is 1.

Aspects of the present invention include a compound of Formula (Ia):

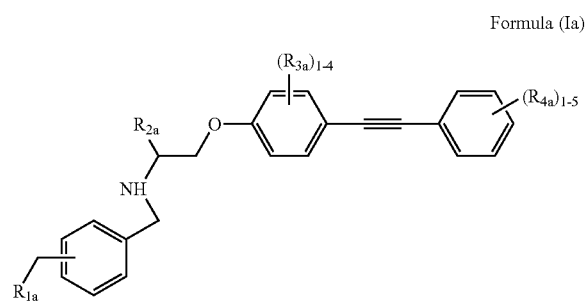

Formula (Ia)

wherein $R_{1a}$ is $NR_{5a}R_{6a}$;

$R_{5a}$ is hydrogen, $(C_{1-10})$alkanyl-$R_{7a}$ or aryl;

$R_{6a}$ is hydrogen or $(C_{1-4})$alkanyl-$R_{7a}$;

$R_{7a}$ is hydrogen, OC(O)—$R_{a1}$, $NH_2$, NH($C_{1-4}$alkanyl), N($C_{1-4}$alkanyl)$_2$ or $R_{a1}$;

$R_{a1}$ is cyclic heteroalkyl-$(R_{12a})_q$ or aryl;

$(R_{12a})_q$ is hydrogen or $(C_{1-4})$alkanyl;

$R_{2a}$ is hydrogen or $(C_{1-4})$alkanyl-$R_{7a}$;

$R_{3a}$ and $R_{4a}$ are independently hydrogen, $(C_{1-4})$alkanyl-$R_{7a}$ or halogen; and, q is 1;

and enantiomers, diastereomers, tautomers, solvates, and pharmaceutically acceptable salts thereof.

Aspects of the present invention include a compound of Formula (Ib):

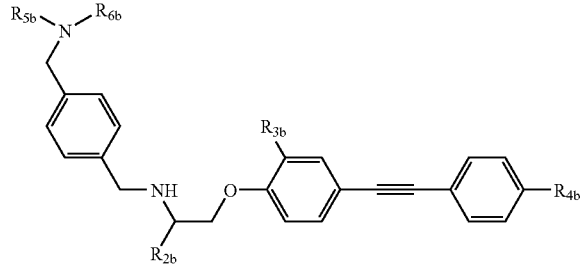

Formula (Ib)

wherein
$R_{5b}$ is hydrogen, $(C_{1-10})$alkanyl-$R_{7b}$ or phenyl;
$R_{6b}$ is hydrogen or $(C_{1-4})$alkanyl-$R_{7b}$;
$R_{7b}$ is hydrogen, OC(O)—$R_{a2}$, $N(C_{1-4}$alkanyl$)_2$ or $R_{a2}$;
$R_{a2}$ is pyrrolidinyl-$(R_{12b})_q$, piperidinyl-$(R_{12b})_q$, morpholinyl-$(R_{12b})_q$ or phenyl; $(R_{12b})_q$ is hydrogen or $(C_{1-4})$alkanyl;
$R_{2b}$ is hydrogen or $(C_{1-4})$alkanyl-$R_{7b}$;
$R_{3b}$ and $R_{4b}$ are independently hydrogen, $(C_{1-4})$alkanyl-$R_{7b}$, chlorine or fluorine; and,
q is 1;

and enantiomers, diastereomers, tautomers, solvates, and pharmaceutically acceptable salts thereof.

Aspects of the present invention include a composition comprising a compound of Formula (Ib) wherein the compound is selected from the group consisting of a compound of Formula (Ib) wherein $R_{2b}$ is Me, $R_{3b}$ is Me, $R_{4b}$ is Cl, $R_{5b}$ is H and $R_{6b}$ is H;
a compound of Formula (Ib) wherein $R_{2b}$ is H, $R_{3b}$ is H, $R_{4b}$ is Cl, $R_{5b}$ is propyl and $R_{6b}$ is H;
a compound of Formula (Ib) wherein $R_{2b}$ is H, $R_{3b}$ is Me, $R_{4b}$ is Cl, $R_{5b}$ is propyl and $R_{6b}$ is H;
a compound of Formula (Ib) wherein $R_{2b}$ is H, $R_{3b}$ is H, $R_{4b}$ is Cl, $R_{5b}$ is isopropyl and $R_{6b}$ is H;
a compound of Formula (Ib) wherein $R_{2b}$ is H, $R_{3b}$ is H, $R_{4b}$ is Cl, $R_{5b}$ is isopentyl and $R_{6b}$ is H;
a compound of Formula (Ib) wherein $R_{2b}$ is H, $R_{3b}$ is Me, $R_{4b}$ is Cl, $R_{5b}$ is isopentyl and $R_{6b}$ is H;
a compound of Formula (Ib) wherein $R_{2b}$ is H, $R_{3b}$ is H, $R_{4b}$ is Cl, $R_{5b}$ is propyl-N(Me)$_2$ and $R_{6b}$ is H;
a compound of Formula (Ib) wherein $R_{2b}$ is H, $R_{3b}$ is Me, $R_{4b}$ is Cl, $R_{5b}$ is benzyl and $R_{6b}$ is H;
a compound of Formula (Ib) wherein $R_{2b}$ is H, $R_{3b}$ is Me, $R_{4b}$ is Cl, $R_{5b}$ is heptyl and $R_{6b}$ is H;
a compound of Formula (Ib) wherein $R_{2b}$ is H, $R_{3b}$ is Me, $R_{4b}$ is Cl, $R_{5b}$ is propyl-Ph and $R_{6b}$ is H;
a compound of Formula (Ib) wherein $R_{2b}$ is H, $R_{3b}$ is Me, $R_{4b}$ is Cl, $R_{5b}$ is decyl and $R_{6b}$ is H;
a compound of Formula (Ib) wherein $R_{2b}$ is H, $R_{3b}$ is Me, $R_{4b}$ is Cl, $R_{5b}$ is hexyl and $R_{6b}$ is H;
a compound of Formula (Ib) wherein $R_{2b}$ is H, $R_{3b}$ is Me, $R_{4b}$ is Cl, $R_{5b}$ is ethyl-2-(1-Me)pyrrolidinyl and $R_{6b}$ is H;
a compound of Formula (Ib) wherein $R_{2b}$ is H, $R_{3b}$ is Me, $R_{4b}$ is Cl, $R_{5b}$ is ethyl-1-pyrrolidinyl and $R_{6b}$ is H;
a compound of Formula (Ib) wherein $R_{2b}$ is H, $R_{3b}$ is Me, $R_{4b}$ is Cl, $R_{5b}$ is propyl-4-morpholinyl and $R_{6b}$ is H;
a compound of Formula (Ib) wherein $R_{2b}$ is H, $R_{3b}$ is Me, $R_{4b}$ is Cl, $R_{5b}$ is ethyl-4-morpholinyl and $R_{6b}$ is H;
a compound of Formula (Ib) wherein $R_{2b}$ is H, $R_{3b}$ is Me, $R_{4b}$ is Cl, $R_{5b}$ is Ph and $R_{6b}$ is H;
a compound of Formula (Ib) wherein $R_{2b}$ is H, $R_{3b}$ is Me, $R_{4b}$ is Cl, $R_{5b}$ is propyl-OC(O)-2-piperidinyl and $R_{6b}$ is H;
a compound of Formula (Ib) wherein $R_{2b}$ is H, $R_{3b}$ is Me, $R_{4b}$ is Cl, $R_{5b}$ is t-butyl and $R_{6b}$ is H;
a compound of Formula (Ib) wherein $R_{2b}$ is H, $R_{3b}$ is Me, $R_{4b}$ is Cl, $R_{5b}$ is n-butyl and $R_{6b}$ is Me;
a compound of Formula (Ib) wherein $R_{2b}$ is H, $R_{3b}$ is Me, $R_{4b}$ is Cl, $R_{5b}$ is H and $R_{6b}$ is H;
a compound of Formula (Ib) wherein $R_{2b}$ is Me, $R_{3b}$ is Cl, $R_{4b}$ is H, $R_{5b}$ is H and $R_{6b}$ is H;
a compound of Formula (Ib) wherein $R_{2b}$ is ethyl, $R_{3b}$ is Me, $R_{4b}$ is Cl, $R_{5b}$ is H and $R_{6b}$ is H;
a compound of Formula (Ib) wherein $R_{2b}$ is Me, $R_{3b}$ is Cl, $R_{4b}$ is Me, $R_{5b}$ is H and $R_{6b}$ is H;
a compound of Formula (Ib) wherein $R_{2b}$ is Me, $R_{3b}$ is Cl, $R_{4b}$ is Cl, $R_{5b}$ is H and $R_{6b}$ is H; and,
a compound of Formula (Ib) wherein $R_{2b}$ is Me, $R_{3b}$ is Cl, $R_{4b}$ is F, $R_{5b}$ is H and $R_{6b}$ is H.

The compounds of the present invention may also be present in the form of pharmaceutically acceptable salts. For use in medicine, the salts of the compounds of this invention refer to non-toxic "pharmaceutically acceptable salts" (Ref. *International J. Pharm.*, 1986, 33, 201-217; *J. Pharm. Sci.*, 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

The processes for the preparation of the compounds according to the invention may give rise to products with tautomeric structural forms; wherein, the structures differ in the point of attachment of a hydrogen atom and exist in an equilibrium favoring the weaker acid. Such products include both keto-enol tautomers and imine-enamine tautomers and are intended to be encompassed within the scope of this invention. Keto-enol tautomers refer to those compound structures wherein a hydroxy atom bonded to an alkenyl carbon (the stronger acid "enol" structure) exists in equilibrium with an oxygen atom bonded by a double-bond to an alkanyl carbon (the weaker acid "keto" structure). Imine-enamine tautomers refer to those compound structures wherein a hydrogen substituted nitrogen atom bonded to an alkenyl carbon (the stronger acid "enamine" structure) exists in equilibrium with a nitrogen atom bonded via a double-bond to an alkanyl carbon (the weaker acid "imine" structure).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

An aspect of the present invention includes a method for treating or ameliorating a reactive oxygen species mediated inflammatory disorder in a subject in need thereof comprising administering to the subject a therapeutically effective amount of an instant compound or pharmaceutical composition thereof. A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as vanilloid receptor modulators is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In the method for treating or ameliorating a reactive oxygen species mediated inflammatory disorder, the term "reactive oxygen species" includes, and is not limited to, a reactive oxygen species selected from a superoxide, hydrogen peroxide, hydroxyl radical or HOCl reactive oxygen species.

By way of example only, the compounds of Formula (I) are useful for treating or ameliorating inflammatory disorders including, but not limited to, a phosphorylation mediated disorder, a polymorphonuclear leucocyte mediated disorder, a macrophage mediated disorder, a lipopolysaccharide mediated disorder, a tumor necrosis factor-α mediated disorder, a cytokine IFN-γ mediated disorder, an interleukin-2 mediated disorder, inflammatory arthritis, potassium peroxochromate arthritis, rheumatoid arthritis, osteoarthritis or Alzheimer's disease.

The terms used in describing the invention are commonly used and known to those skilled in the art. As used herein, the following abbreviations have the indicated meanings:

| | | |
|---|---|---|
| DEAD | diethylazodicarboxylate | |
| DIBAL | diisobutylaluminum hydride | |
| TPP | triphenylphosphine | |
| mp | melting point | |
| HBSS | | |
| h | Hour | |
| min | Minute | |
| rt | Room temperature | |

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Scheme A

Compound A3 was synthesized by reacting Compound A1 with Compound A2 in a solvent such as acetone or acetonitrile in the presence of potassium carbonate at elevated temperature. A palladium(II) catalyst such as bis(acetato)bis (triphenylphosphine)palladium(II) and a base such as triethylamine palladium were used to couple Compound A3 with Compound A4 at elevated temperature to afford Compound A5. Reductive amination of Compound A5 with Compound A6 and a reducing agent such as NaBH(OAc)$_3$ (sodium triacetoxyborohydride) provided the target Compound A7 of Formula (I).

Scheme A:

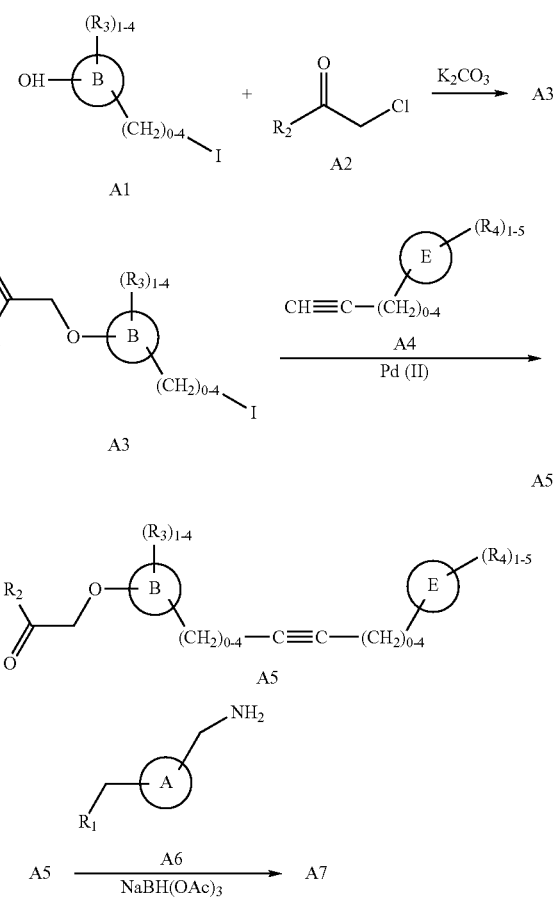

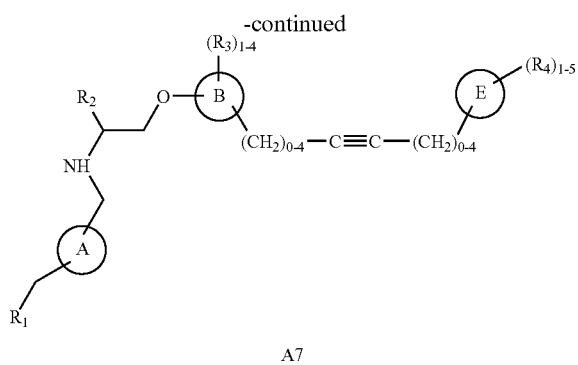

A7

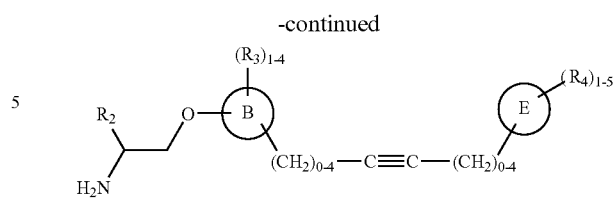

B4

Scheme B

Alternatively, a target Compound B8 of Formula (I), wherein $R_1$ is $NR_5R_6$, may be produced using the method of Scheme B. Compound A1 was reacted with Compound B1 using triphenylphosphine (TPP) and a coupling reagent such as diisopropylazodicarboxylate (DIAD) in a suitable solvent such as acetonitrile to give Compound B2. Deprotection of the amine Compound B2 was accomplished using hydrazine in a refluxing solvent such as ethanol to give the free amine Compound B3. Palladium catalyzed coupling of Compound B3 with Compound A4 provided Compound B4. Reductive amination of Compound B4 with Compound B5 and a reducing agent such as $NaBH(OAc)_3$ afforded Compound B6. Acidic hydrolysis of the acetal Compound B6 gave an aldehyde Compound B7. A final reductive amination with a desired substituted or unsubstituted amine and $NaBH(OAc)_3$ gave the target Compound B8.

Scheme B:

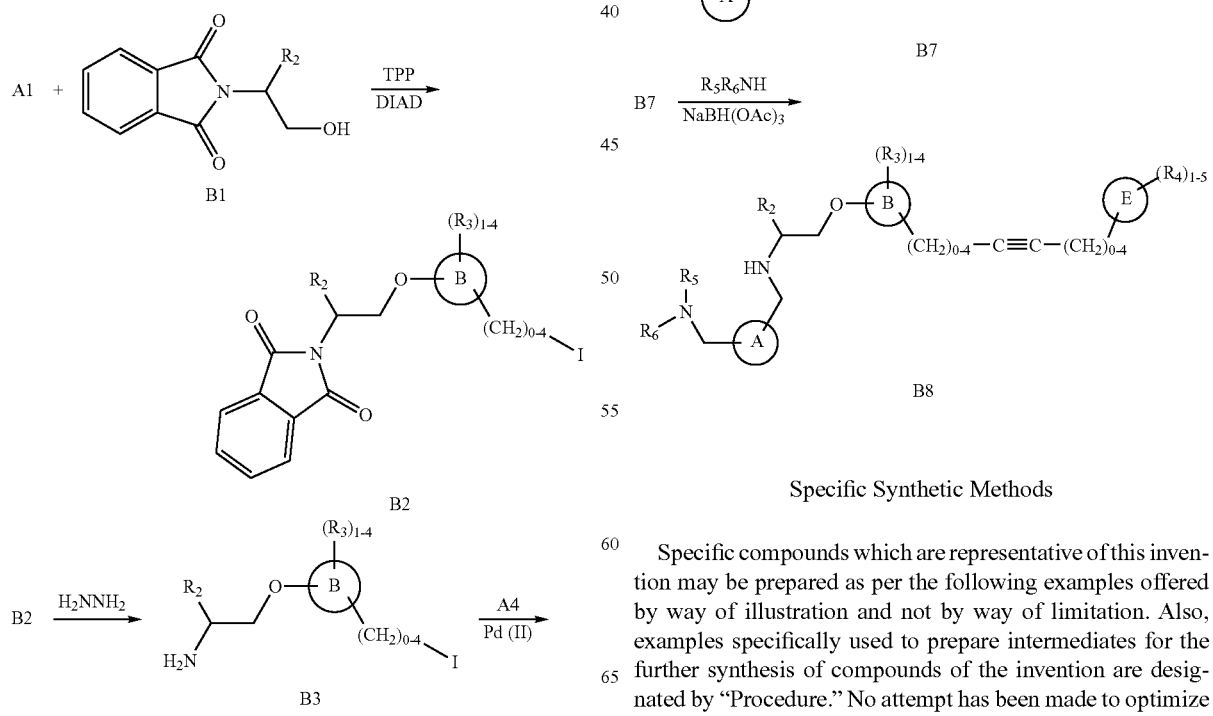

Specific Synthetic Methods

Specific compounds which are representative of this invention may be prepared as per the following examples offered by way of illustration and not by way of limitation. Also, examples specifically used to prepare intermediates for the further synthesis of compounds of the invention are designated by "Procedure." No attempt has been made to optimize the yields obtained in any of the reactions. One skilled in the art would know how to increase such yields through routine variations in reaction times, temperatures, solvents and/or reagents.

EXAMPLE 1

N-[2-[4-[(4-chlorophenyl)ethynyl]-2-methylphenoxy]-1-methylethyl]-1,4-benzenedimethanamine (Compound 1)

A mixture of Compound 1a (5.32 g, 22.7 mmol), Compound 1b (1.90 mL, 23.9 mmol), potassium carbonate (5.24 g, 37.9 mmol) and sodium iodide (cat.) was stirred in acetone (200 mL) at reflux for 18 hours. The mixture was then cooled, filtered and the solids washed with additional acetone (30 mL). The filtrate was then evaporated in vacuo and the residue dissolved in ethyl acetate (100 mL) and washed with 1N sodium hydroxide (50 mL) then water (50 mL). The organic layer was dried over sodium sulfate, filtered and evaporated in vacuo to give Compound 1c as a tan solid. Mp 86-88.5° C.; $^1$H NMR (CDCl$_3$) δ 7.48 (s, 1H), 7.44 (d, 1H), 6.42 (d, 1H), 4.50 (s, 2H), 2.30 (s, 3H), 2.25 (s, 3H). A mixture of Compound 1c (1.00 g, 3.45 mmol), triethylamine (50 mL), Compound 1d (71 g, 5.17 mmol) and bis(acetato)bis(triphenylphosphine)palladium(II) (10 mol %) was placed in a 200 mL round bottom flask. The mixture was stirred at 70° C. for 5 hours then concentrated in vacuo. The residue was purified using silica gel flash chromatography eluting with ethyl acetate/hexane (1:1) to give Compound 1e as a brown solid. Mp 86-90° C.; $^1$H NMR (CDCl$_3$) δ 4.55 (s, 2H), 2.32 (s, 3H), 2.30 (s, 3H).

Compound 1e (17.34 g, 58.04 mmol) was dissolved in methylene chloride (525 mL) and p-xylylene diamine (19.56 g, 143.61 mmol), sodium triacetoxyborohydride (18.45 g, 87.06 mmol) and acetic acid (5 mL) were added. The resulting mixture was stirred under a nitrogen atmosphere at ambient temperature for 17 hours. An aqueous solution of 1N sodium hydroxide (450 mL) was then added and the mixture was stirred for an additional hour before separating the layers. The organic layer was concentrated and the residue was chromatographed on a silica gel column eluting with methylene chloride/methanol/triethylamine (95:5:0.5). The product was then dissolved in methylene chloride and washed with 1N sodium hydroxide. The organic layer was dried over sodium sulfate and evaporated in vacuo to give Compound 1 as a brown gum. $^1$H NMR (CDCl$_3$) δ 3.09-3.26 (m, 1H), 2.21 (s, 3H), 1.21 (d, 3H). The di-HCl salt of Compound 1 was prepared by dissolving the free base (8.66 g, 20.67 mmol) in 1,4-dioxane (10 mL), a solution of 4N HCl in dioxane (80 mL) was then added. The resulting solution was evaporated in vacuo to dryness and the solid was triturated in ether and filtered to give the desired HCl salt. Mp>300° C.; MS 419 (MH$^+$); $^1$H NMR (DMSO) δ 3.48-3.63 (m, 1H), 2.24 (s, 3H), 1.47 (d, 3H). Calculated for C$_{26}$H$_{29}$Cl$_3$N$_2$O ¼ hydrate: C, 62.91; H, 5.99; N, 5.64. Found: C, 62.87; H, 5.96; N, 5.48.

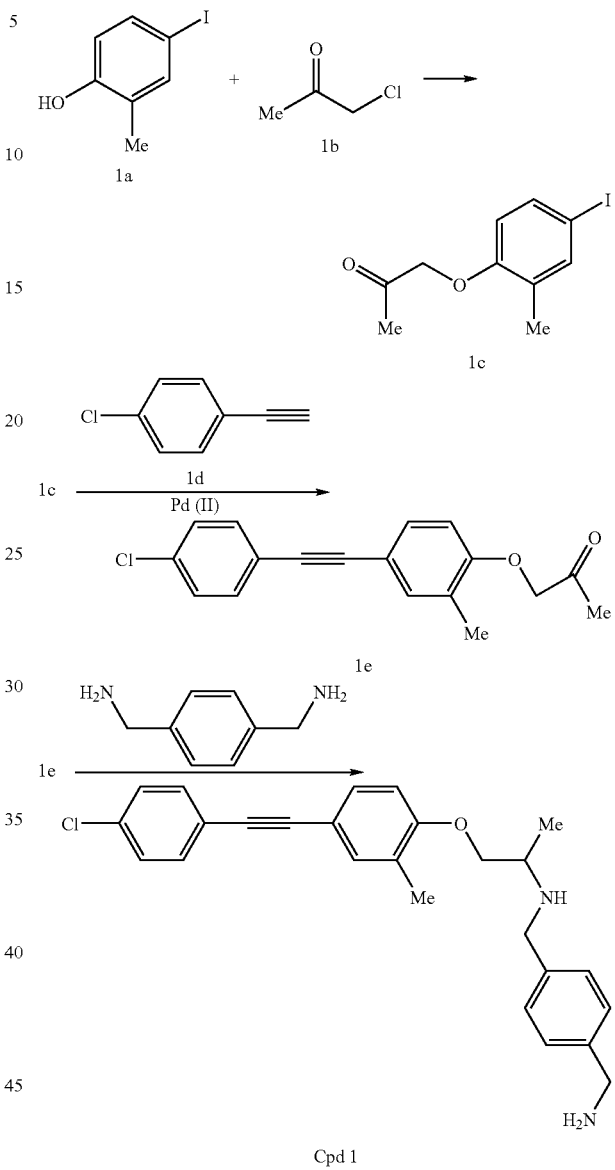

Cpd 1

Using the procedure of Example 1 and the appropriate reagents and starting materials known to those skilled in the art, other compounds of the present invention may be prepared including, but not limited to:

| Cpd | Name | m.p. (° C.) | MS (MH$^+$) |
|---|---|---|---|
| 22 | N-[2-[2-chloro-4-(phenylethynyl)phenoxy]-1-methylethyl]-1,4-benzenedimethanamine<br>The free base was obtained as a red oil | — | 405 |
| 23 | N-[1-[[4-[(4-chlorophenyl)ethynyl]-2-methylphenoxy]methyl]propyl]-1,4-benzenedimethanamine<br>The free base was obtained as a yellow gum[1]; the Di-HCl salt[2] was also prepared | 261.5-264° C.[2] | 433[1] |

-continued

| Cpd | Name | m.p. (° C.) | MS (MH+) |
|---|---|---|---|
| 24 | N-[2-[2-chloro-4-[(4-methylphenyl)ethynyl]phenoxy]-1-methylethyl]-1,4-benzenedimethanamine Prepared as the Di-HCl salt | >300 | 419 |
| 25 | N-[2-[2-chloro-4-[(4-chlorophenyl)ethynyl]phenoxy]-1-methylethyl]-1,4-benzenedimethanamine Prepared as the Di-HCl salt | >300 | 439 |
| 26 | N-[2-[2-chloro-4-[(4-fluorophenyl)ethynyl]phenoxy]-1-methylethyl]-1,4-benzenedimethanamine Prepared as the Di-HCl salt | >300 | 423 |

EXAMPLE 2

$N^1$-[2-[4-[(4-chlorophenyl)ethynyl]phenoxy]ethyl]-$N^4$-propyl-1,4-benzenedimethanamine (Compound 2)

Compound 2a (8.23 g, 37.4 mmol) was dissolved in acetonitrile (200 mL) and Compound 2b (7.15 g, 37.4 mmol), diisopropylazodicarboxylate (8.8 mL, 44.9 mmol) and triphenylphosphine (11.77 g, 44.9 mmol) were then added. After 4 hours ether (50 mL) was added and the solid was collected by filtration to give Compound 2c, which was used without further purification. Mp 180-181.5° C.; $^1$H NMR (CDCl$_3$) δ 4.23 (t, 2H), 4.13 (t, 2H). Compound 2c (3.00 g, 7.63 mmol) was stirred in methanol and hydrazine monohydrate (1.50 mL) was added. The mixture was heated to reflux for 3 hours then evaporated in vacuo. Aqueous potassium hydroxide (5N, 150 mL) was added and the mixture was extracted with methylene chloride. The organic layer was washed with water, dried over sodium sulfate and evaporated in vacuo to give Compound 2d as a white solid. MS 264 (MH+); $^1$H NMR (CDCl$_3$) δ 7.54 (d, 2H), 6.70 (d, 2H), 3.95 (t, 2H), 3.08 (t, 2H).

Compound 2d (6.62 g, 25.16 mmol) was dissolved in triethylamine (250 mL). Bis(acetato)bis(triphenylphosphine)palladium(II) (1.88 g, 10 mol %) and Compound 1d (5.16 g, 37.75 mmol) were added. The resulting mixture was stirred at 70° C. for 5 hours and evaporated in vacuo. The crude solid was slurried in methylene chloride and washed with 1N sodium hydroxide then water. The organic layer was evaporated and the residue triturated with ether/hexane (1:1) to give Compound 2e as a tan solid. MS 271.9 (MH+). Compound 2e (1.99 g, 7.32 mmol) was dissolved in methylene chloride (120 mL). Compound 2f (1.32 mL, 6.66 mmol), sodium triacetoxyborohydride (2.12 g, 9.99 mmol) and acetic acid (0.40 mL) were added. The mixture was stirred for 24 hours before adding 1N aqueous sodium hydroxide (30 mL). The organic layer was dried over sodium sulfate and concentrated. The product was purified on a silica gel column eluting with methylene chloride/methanol (19:1) to give Compound 2g as a yellow gum. MS 465 (MH+); $^1$H NMR (CDCl$_3$) δ 5.49 (s, 1H), 4.10 (t, 2H), 3.89 (s, 2H), 3.04 (t, 2H), 1.24 (t, 6H).

Compound 2g (4.96 g, 10.69 mmol) was dissolved in a mixture of acetic acid and water (5:1, 60 mL). The mixture was stirred at 70° C. for 3 hours before being poured into ice. The solution was neutralized with 1N sodium hydroxide to pH 7 and the product was extracted with ethyl acetate. The organic layer was evaporated and the residue was triturated in water to give Compound 2h as a tan solid. MS 390 (MH+); $^1$H NMR (CDCl$_3$) δ 10.02 (s, 1H), 4.13 (t, 2H), 3.99 (s, 2H), 3.06 (t, 2H). Compound 2h (0.500 g, 1.28 mmol) was dissolved in methylene chloride (50 mL). Propylamine (0.12 mL, 1.41 mmol), sodium triacetoxyborohydride (0.41 g, 1.92 mmol) and acetic acid (0.30 mL) were added. The mixture was stirred for 24 hours before adding 1N aqueous sodium hydroxide (30 mL). The organic layer was concentrated and the residue was chromatographed on a silica gel column eluting with methylene chloride/methanol/triethylamine (9:1:0.05). The fractions containing the product were combined and concentrated to 50 mL and washed with 1N aqueous sodium hydroxide (30 mL). The organic layer was dried over sodium sulfate, filtered and evaporated in vacuo to give Compound 2 as a yellow gum. MS 433; $^1$H NMR (CDCl$_3$) δ 4.10 (t, 2H), 3.86 (s, 2H), 3.78 (s, 2H), 3.03 (t, 2H), 2.59 (t, 2H), 1.53 (q, 2H), 0.92 (t, 3H).

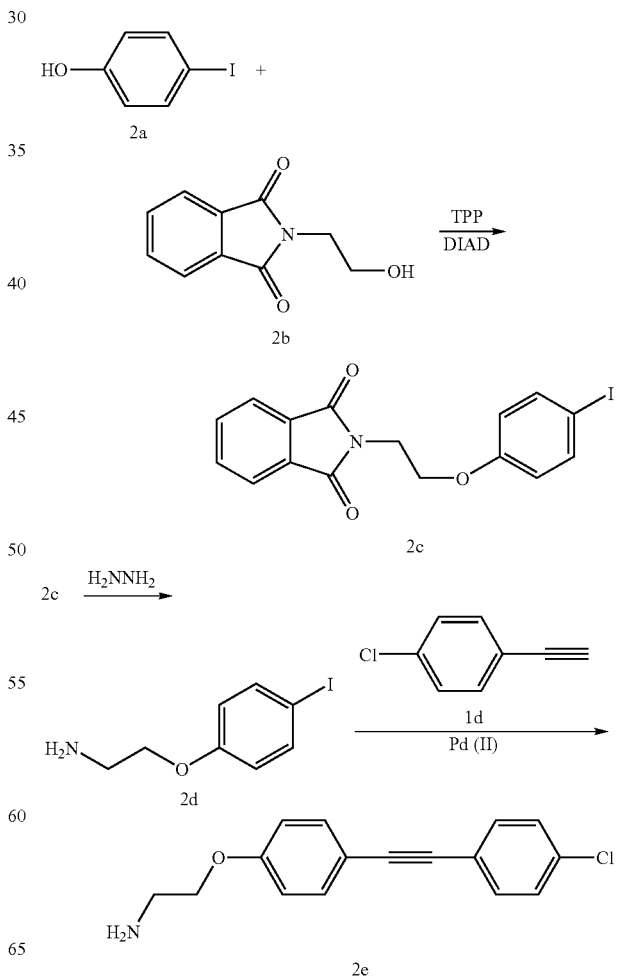

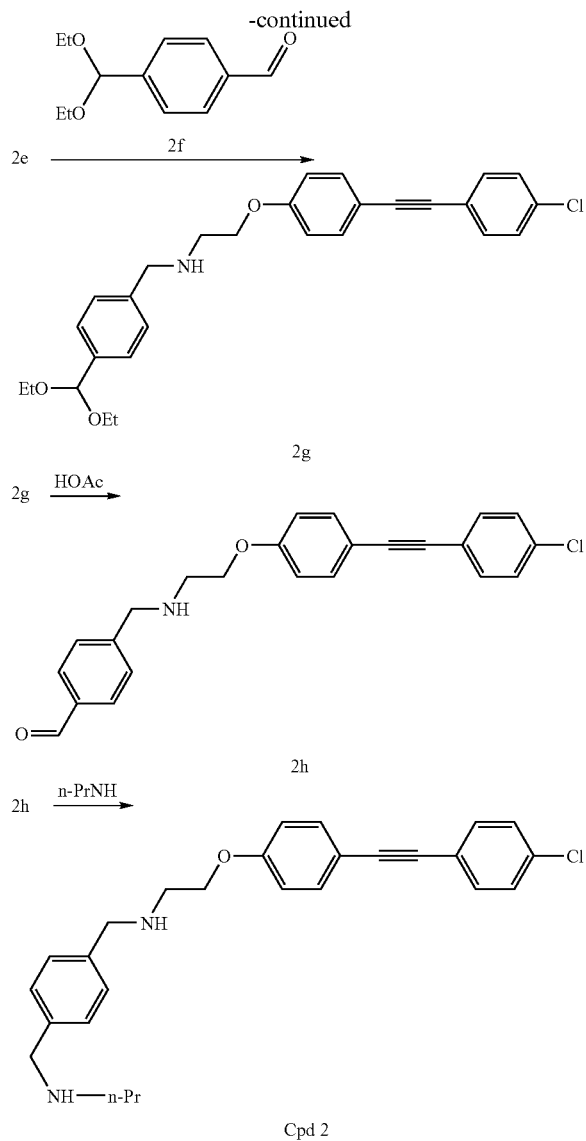

obtained as a yellow gum. MS 433; $^1$H NMR (CDCl$_3$) δ 4.10 (t, 2H), 3.86 (d, 2H, becomes singlet with D$_2$O exchange), 2.80 (m, 1H), 1.09 (d, 6H).

EXAMPLE 5

N$^1$-[2-[4-[(4-chlorophenyl)ethynyl]phenoxy]ethyl]-N$^4$-(3-methylbutyl)-1,4-benzenedimethanamine (Compound 5)

Compound 5 was synthesized using the procedure described for Compound 2 except that isoamylamine was used in the final reductive amination step. Compound 5 was obtained as a white solid. MS 462; $^1$H NMR (CDCl$_3$) δ 4.10 (t, 2H), 3.86 (s, 2H), 3.77 (s, 2H), 3.03 (t, 2H), 2.63 (t, 2H), 0.89 (d, 6H).

EXAMPLE 6

N$^1$-[2-[4-[(4-chlorophenyl)ethynyl]-2-methylphenoxy]ethyl]-N$^4$-(3-methylbutyl)-1,4-benzenedimethanamine (Compound 6)

Compound 6 was synthesized following the procedure described for Compound 5 except that Compound 1a was used as starting material. Compound 6 was obtained as a yellow gum. MS 475, 477; $^1$H NMR (CDCl$_3$) δ 4.11 (t, 2H), 3.88 (s, 2H), 2.64 (t, 2H), 2.21 (s, 3H), 0.89 (d, 6H).

EXAMPLE 7

N$^1$-[2-[4-[(4-chlorophenyl)ethynyl]phenoxy]ethyl]-N$^4$-[3-(dimethylamino)propyl]-1,4-benzenedimethanamine (Compound 7)

Compound 7 was synthesized following the procedure described for Compound 2 except that (3-dimethylamino) propoylamine was used in the final reductive amination step. Compound 7 was obtained as a white gum. MS 477 (MH$^+$); $^1$H NMR (CDCl$_3$) δ 4.10 (t, 2H), 3.86 (s, 2H), 3.78 (s, 2H), 3.03 (t, 2H), 2.66 (t, 2H), 2.31 (t, 2H), 2.21 (s, 6H).

EXAMPLE 8

N$^1$-[2-[4-[(4-chlorophenyl)ethynyl]-2-methylphenoxy]ethyl]-N$^4$-(phenylmethyl)-1,4-benzenedimethanamine (Compound 8)

Compound 8 was synthesized following the procedure described for Compound 2 except that Compound 1a was used as the starting material and benzylamine was used for the final reductive amination step. Compound 8 was obtained as a yellow gum. MS 495, 497; $^1$H NMR (CDCl$_3$) δ 4.11(t, 2H), 3.88 (s, 2H), 3.06 (t, 2H), 2.21 (s, 3H).

EXAMPLE 3

N$^1$-[2-[4-[(4-chlorophenyl)ethynyl]-2-methylphenoxy]ethyl]-N$^4$-propyl-1,4-benzenedimethanamine (Compound 3)

Compound 3 was synthesized following the procedure described for Compound 2 with an exception that Compound 1a was used as starting material. Compound 3 was obtained as a gum. MS 447.

EXAMPLE 4

N$^1$-[2-[4-[(4-chlorophenyl)ethynyl]phenoxy]ethyl]-N$^4$-(1-methylethyl)-1,4-benzenedimethanamine (Compound 4)

Compound 4 was synthesized using the procedure described for Compound 2 except that isopropylamine was used in the last reductive amination step. Compound 4 was

EXAMPLE 9

N$^1$-[2-[4-[(4-chlorophenyl)ethynyl]-2-methylphenoxy]ethyl]-N$^4$-heptyl-1,4-benzenedimethanamine (Compound 9)

Compound 9 was synthesized following the procedure described for Compound 2 except that Compound 1a was used as the starting material and heptylamine was used for the final reductive amination step. Compound 9 was obtained as a yellow gum. MS 503, 504, 505; $^1$H NMR (CDCl$_3$) δ 4.11 (t, 2H), 3.88 (s, 2H), 3.77 (s, 2H), 3.05 (t, 2H), 2.62 (t, 2H), 2.21 (s, 3H), 0.87 (t, 3H).

EXAMPLE 10

N$^1$-[2-[4-[(4-chlorophenyl)ethynyl]-2-methylphenoxy]ethyl]-N$^4$-(3-phenylpropyl)-1,4-benzenedimethanamine (Compound 10)

Compound 10 was synthesized following the procedure described for Compound 2 except that Compound 1a was used as the starting material and (3-phenyl)propylamine was used for the final reductive amination step. Compound 10 was obtained as yellow oil. MS 523, 524, 525; $^1$H NMR (CDCl$_3$) δ 4.11 (t, 2H), 3.88 (s, 2H), 3.77 (s, 2H), 3.05 (t, 2H), 2.21 (s, 3H).

EXAMPLE 11

N$^1$-[2-[4-[(4-chlorophenyl)ethynyl]-2-methylphenoxy]ethyl]-N$^4$-decyl-1,4-benzenedimethanamine (Compound 11)

Compound 11 was synthesized following the procedure described for Compound 2 except that Compound 1a was used as the starting material and decylamine was used for the final reductive amination step. Compound 11 was obtained as a yellow gum. MS 545, 546, 547; $^1$H NMR (CDCl$_3$) δ 4.11 (t, 2H), 3.88 (s, 2H), 3.77 (s, 2H), 3.05 (t, 2H), 2.62 (t, 2H), 2.21 (s, 3H).

EXAMPLE 12

N$^1$-[2-[4-[(4-chlorophenyl)ethynyl]-2-methylphenoxy]ethyl]-N$^4$-hexyl-1,4-benzenedimethanamine (Compound 12)

Compound 12 was synthesized following the procedure described for Compound 2 except that Compound 1a was used as the starting material and hexylamine was used for the final reductive amination step. Compound 12 was obtained as a yellow gum. MS 489, 490, 491; $^1$H NMR (CDCl$_3$) δ 4.11 (t, 2H), 3.88(s, 2H), 3.78(s, 2H), 3.05 (t, 2H), 2.62 (t, 2H).

EXAMPLE 13

N$^1$-[2-[4-[(4-chlorophenyl)ethynyl]-2-methylphenoxy]ethyl]-N$^4$-[2-(1-methyl-2-pyrrolidinyl)ethyl]-1,4-benzenedimethanamine (Compound 13)

Compound 13 was synthesized following the procedure described for Compound 2 except that Compound 1a was used as the starting material and 2-(1-methyl-2-pyrrolidinyl)ethylamine was used for the final reductive amination step. Compound 13 was obtained as a yellow gum. MS 516, 518, 519; $^1$H NMR (CDCl$_3$) δ 4.11 (t, 2H), 3.88 (d, 2H), 3.78 (s, 2H), 2.30 (s, 3H), 2.21 (s, 3H). The tri HCl salt of Compound 13 prepared using the procedure described in Example 1 was obtained as a yellow solid: Mp 251-254° C.; Calculated for C$_{32}$H$_{41}$Cl$_4$N$_3$O H$_2$O: C, 59.73; H, 6.74; N, 6.53; Found: C, 59.39; H, 6.88; N, 6.27.

EXAMPLE 14

N$^1$-[2-[4-[(4-chlorophenyl)ethynyl]-2-methylphenoxy]ethyl]-N$^4$-[2-(1-pyrrolidinyl)ethyl]-1,4-benzenedimethanamine (Compound 14)

Compound 14 was synthesized following the procedure described for Compound 2 except that Compound 1a was used as the starting material and 2-pyrrolidinylethylamine was used for the final reductive amination step. Compound 14 was obtained as yellow oil. MS 502, 503, 504; $^1$H NMR (CDCl$_3$) δ 4.11 (t, 2H), 3.88 (s, 2H), 3.80 s, 2H), 3.05 (t, 2H), 2.74(t, 2H), 2.61 (t, 2H), 2.21 (s, 3H),

EXAMPLE 15

N$^1$-[2-[4-[(4-chlorophenyl)ethynyl]-2-methylphenoxy]ethyl]-N$^4$-[3-(4-morpholinyl)propyl]-1,4-benzenedimethanamine (Compound 15)

Compound 15 was synthesized following the procedure described for Compound 2 except that Compound 1a was used as the starting material and 3-morpholinopropylamine was used for the final reductive amination step. Compound 15 was obtained as a yellow gum. MS 532, 533, 534; $^1$H NMR (CDCl$_3$) δ 4.11 (t, 2H), 3.88 (s, 2H), 3.77(s, 2H), 3.70 (t, 4H), 3.05 (t, 2H), 2.68 (t, 2H), 2.21 (s, 3H).

EXAMPLE 16

N$^1$-[2-[4-[(4-chlorophenyl)ethynyl]-2-methylphenoxy]ethyl]-N$^4$-[2-(4-morpholinyl)ethyl]-1,4-benzenedimethanamine (Compound 16)

Compound 16 was synthesized following the procedure described for Compound 2 except that Compound 1a was used as the starting material and 2-morpholinoethylamine was used for the final reductive amination step. Compound 16 was obtained as a yellow gum. MS 518, 519, 520; $^1$H NMR (CDCl$_3$) δ 4.11 (t, 2H), 3.88 (s, 2H), 3.79 (s, 2H), 3.69 (t, 4H), 3.06(t, 2H), 2.70 (t, 2H), 2.50 (t, 2H), 2.40 (t, 4H), 2.21 (s, 3H).

EXAMPLE 17

N$^1$-[2-[4-[(4-chlorophenyl)ethynyl]-2-methylphenoxy]ethyl]-N$^4$-phenyl-1,4-benzenedimethanamine (Compound 17)

Compound 17 was synthesized following the procedure described for Compound 2 except that Compound 1a was used as the starting material and phenylamine was used for the final reductive amination step. Compound 17 was obtained as a dark yellow gum. MS 481, 482, 483; $^1$H NMR (CDCl$_3$) δ 4.32 (d, 2H, becomes singlet upon D$_2$O exchange), 4.11 (t, 2H), 3.88 (s, 2H), 3.06 (t, 2H), 2.21 (s, 3H).

EXAMPLE 18

3-[[[4-[[[2-[4-[(4-chlorophenyl)ethynyl]-2-methylphenoxy]ethyl]amino]methyl]phenyl]methyl]amino]propyl ester 2-piperidinecarboxylic acid (Compound 18)

Compound 18 was synthesized following the procedure described for Compound 2 except that Compound 1a was used as the starting material and 3-propyl-2-pipecolinylamine was used for the final reductive amination step. Compound 18 was obtained as a yellow gum. MS 544, 545, 546; $^1$H NMR (CDCl$_3$) δ 4.11 (t, 2H), 3.88 (s, 2H), 3.77 (s, 2H), 3.05 (t, 2H), 2.63 (t, 2H), 2.21 (s, 3H), 1.04 (d, 3H).

EXAMPLE 19

N$^1$-[2-[4-[(4-chlorophenyl)ethynyl]-2-methylphenoxy]ethyl]-N$^4$-(1,1-dimethylethyl)-1,4-benzenedimethanamine (Compound 19)

Compound 19 was synthesized following the procedure described for Compound 2 except that Compound 1a was used as the starting material and t-butylamine was used for the final reductive amination step. Compound 19 was obtained as a yellow gum. MS 461, 462, 463; $^1$H NMR (CDCl$_3$) δ 4.10 (t, 2H), 3.86 s, 2H), 3.70 (d, 2H), 3.03 (t, 2H), 2.20 (s, 3H), 1.18 (s, 9H).

EXAMPLE 20

N$^1$-butyl-N$^4$-[2-[4-[(4-chlorophenyl)ethynyl]-2-methylphenoxy]ethyl]-1,4-benzenedimethanamine (Compound 20)

Compound 20 was synthesized following the procedure described for Compound 2 except that Compound 1a was used as the starting material and butylmethylamine was used for the final reductive amination step. Compound 20 was obtained as yellow oil. MS 475, 476, 477; $^1$H NMR (CDCl$_3$) δ 4.11 (t, 2H), 3.87 (s, 2H), 3.06 d, 2H), 2.36 t, 2H), 2.21 (s, 3H), 2.18 (s, 3H).

EXAMPLE 21

N-[2-[4-[(4-chlorophenyl)ethynyl]-2-methylphenoxy]ethyl]-1,4-benzenedimethanamine (Compound 21)

A mixture of 2-methyl-4-iodophenol (5.00 grams), 1,2-dibromoethane (2.76 mL), sodium hydroxide (1.3 grams) and ethanol (100 mL) was stirred at reflux for 5 hours before being poured into ice. The crude solid was dissolved in dichloromethane and washed with 1N NaOH. The organic layer was evaporated in vacuo to give 2-Bromo-1-(2-methyl-4-iodophenoxy)ethane Compound 21a as a tan solid. $^1$H NMR (CDCl$_3$) δ 6.54 (d, 1H), 4.25 (t, 2H), 3.66 (t, 2H), 2.20 (s, 3H).

Compound 21a (2.52 grams) was suspended in 75 mL of triethylamine and 1-chloro-4-ethynyl benzene (1.51 grams) and 5 mol % bis(acetato) bis(triphenylphosphine) palladium (II) were added. The mixture was stirred at reflux for 6 hours and then evaporated to give the crude product as a gum. The product was purified on a silica gel column eluted with hexane:ethyl acetate (19:1) to give 2-[4-(4-chlorophenyl)ethynyl-2-methylphenoxy]ethylbromide Compound 21b as a brown gum. $^1$H NMR (CDCl$_3$) δ 4.31 (t, 2H), 3.67 (t, 2H), 2.25 (s, 3H).

A mixture of Compound 21b (2.07 grams), p-xylylenediamine (1.26 grams) and potassium carbonate (1.71 grams) in acetonitrile (75 mL) was stirred at reflux for 8 hours and then evaporated. The residue was partitioned between water and ethyl acetate. The organic layer was concentrated and chromatographed on a silica gel column eluted with dichloromethane:methanol:triethylamine (9:1:0.1) to give Compound 21 as a brown gum. MS 405; $^1$H NMR (CDCl$_3$) δ 4.11 (t, 2H), 3.88 (s, 2H), 3.86 (s, 2H), 3.05 (t, 2H), 2.21 (s, 3H).

BIOLOGICAL EXAMPLES

The compounds of the present invention are useful as inhibitors of a nicotinamide adenine dinucleotide oxidase hydride donor. The following biological examples demonstrate the use of the instant compounds in a method for treating or ameliorating a reactive oxygen species mediated disease.

EXAMPLE 1

Oxidase Inhibition Assay

Whole cells (human neutrophils) are incubated with a pro-inflammatory agonist phorbol myristate acetate (PMA) in the presence or absence of test compound to measure the superoxide-mediated reduction of Cytochrome c at 550 nm. Inhibition of the oxidase is determined by a decreased absorbance at 550 nm, in response to test compound, relative to the absorbance seen with a vehicle control.

Method

The buffy coat from one unit of blood is split evenly into four 50 mL tubes. To each tube 30 mL 3% Dextran (in 0.9% NaCl) is added and the tubes are inverted to mix. Tubes are allowed to sit undisturbed for 25 minutes. The resulting supernatant is recovered into four fresh tubes and centrifuged for 10 minutes at 600×g, 4° C. The supernatant is discarded and pellets are resuspended in 35 mL 0.9% saline. 10 mL Ficoll-Paque PLUS (Pharmacia Biotech AB) is layered beneath the cell suspension and centrifuged at 600×g for 40 minutes at room temperature. The supernatant is again discarded and tubes are tapped to loosen the resulting pellets. 20 mL 0.2% ice cold saline is added for 30 seconds followed by 20 mL 1.6% ice cold saline to lyse the remaining erythrocytes in the pellets. The pellets are centrifuged for 10 minutes at 600×g, 4° C., and the supernatant is discarded. The neutrophil pellets are resuspended in HBSS-glucose buffer (1 mg/mL), adding 2.5 mL to each tube for a total volume of 10 mL. The cell suspension is then counted on a hemocytometer.

The cell suspension is diluted to a concentration of 5×10$^6$/mL in HBSS-glucose and treated with 1 μg/mL Cytochalasin B (5 mg/mL DMSO) for 10 minutes at 37° C. in a shaking water bath. Cells are diluted to 6×10$^5$ cells/mL in 92 μM Cytochrome C for a final concentration of 5×10$^4$ cells/well.

The NADPH-oxidase assay is run on a Biomek 2000 workstation. The workstation adds 2.5 μL compound per well from source plates plus 12.5 μL per well 4 μM PMA (agonist). This volume is brought up to 100 μL total per well in the assay plates upon the addition of the prepared cells (85 μL). The final concentration of drug is 25 μM and PMA is 0.5 μM under these conditions.

The QC curve is a dose-response curve (from about 31.25 nM to about 4000 nM) for competitive binding against a known oxidase inhibitor such as DPI (diphenylene iodonium chloride). The format used for each compound tested is as follows:

| Wells | % Inhibition | Inhibitor | Agent added |
|---|---|---|---|
| A-D | Control wells | 2.5 μL vehicle | 12.5 μL (agonist) |
| E-F | Blank wells | 2.5 μL vehicle | 12.5 μL (HBSS) |
| G-H | ~70% (at 250 nm) | 2.5 μL of 10 μM DPI | 12.5 μL (agonist) |

The plates are incubated for 1 hour at 37° C. without CO$_2$. The plates are then incubated at room temperature for 30 minutes and the absorbance is read at 550 nm. The data for instant compounds of the invention is shown in Table 1.

TABLE 1

| Cpd | IC$_{50}$ (μM) |
|---|---|
| 1 | 0.7 |
| 2 | 2.07 |
| 3 | 1.38 |
| 4 | 1.2 |
| 5 | 2.17 |
| 6 | 2.28 |
| 7 | 0.77 |
| 8 | 3.24 |

TABLE 1-continued

| Cpd | IC$_{50}$ (μM) |
|---|---|
| 9 | 6.66 |
| 10 | 8.34 |
| 12 | 11.13 |
| 13 | 1 |
| 14 | 2.35 |
| 15 | 1.61 |
| 16 | 2.66 |
| 18 | 3.01 |
| 19 | 3.33 |
| 21 | 1.77 |
| 22 | 0.85 |
| 23 | 0.8 |
| 24 | 0.7 |
| 25 | 0.7 |
| 26 | 1.05 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (Ib):

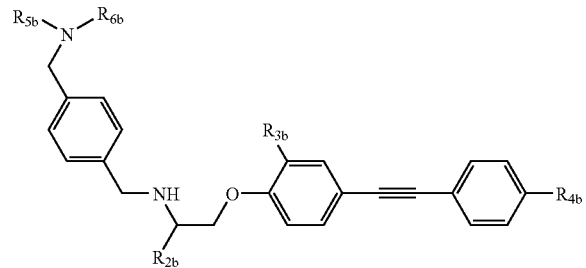

Formula (Ib)

wherein
$R_{5b}$ is hydrogen, $(C_{1-10})$alkanyl-$R_{7b}$ or phenyl;
$R_{6b}$ is hydrogen or $(C_{1-4})$alkanyl-$R_{7b}$;
$R_{7b}$ is hydrogen, OC(O)—$R_{a2}$, N($C_{1-4}$alkanyl)$_2$ or $R_{a2}$;
$R_{a2}$ is pyrrolidinyl-$(R_{12b})_q$, piperidinyl-$(R_{12b})_q$, morpholinyl-$(R_{12b})_q$ or phenyl;
$(R_{12b})_q$ is hydrogen or $(C_{1-4})$alkanyl;
$R_{2b}$ is hydrogen or $(C_{1-4})$alkanyl-$R_{7b}$;
$R_{3b}$ and $R_{4b}$ are independently hydrogen, $(C_{1-4})$alkanyl-$R_{7b}$, chlorine or fluorine; and,
q is 1;
and enantiomers, diastereomers, tautomers, solvates, and pharmaceutically acceptable salts thereof.

2. A compound of Formula (Ib) wherein the compound is selected a compound of Formula (Ib) wherein $R_{2b}$ is Me, $R_{3b}$ is Me, $R_{4b}$ is Cl, $R_{5b}$ is H and $R_{6b}$ is H;
a compound of Formula (Ib) wherein $R_{2b}$ is H, $R_{3b}$ is H, $R_{4b}$ is Cl, $R_{5b}$ is propyl and $R_{6b}$ is H;
a compound of Formula (Ib) wherein $R_{2b}$ is H, $R_{3b}$ is Me, $R_{4b}$ is Cl, $R_{5b}$ is propyl and $R_{6b}$ is H;
a compound of Formula (Ib) wherein $R_{2b}$ is H, $R_{3b}$ is H, $R_{4b}$ is Cl, $R_{5b}$ is isopropyl and $R_{6b}$ is H;
a compound of Formula (Ib) wherein $R_{2b}$ is H, $R_{3b}$ is H, $R_{4b}$ is Cl, $R_{5b}$ is isopentyl and $R_{6b}$ is H;
a compound of Formula (Ib) wherein $R_{2b}$ is H, $R_{3b}$ is Me, $R_{4b}$ is Cl, $R_{5b}$ is isopentyl and $R_{6b}$ is H;
a compound of Formula (Ib) wherein $R_{2b}$ is H, $R_{3b}$ is H, $R_{4b}$ is Cl, $R_{5b}$ is propyl-N(Me)$_2$ and $R_{6b}$ is H;
a compound of Formula (Ib) wherein $R_{2b}$ is H, $R_{3b}$ is Me, $R_{4b}$ is Cl, $R_{5b}$ is benzyl and $R_{6b}$ is H;
a compound of Formula (Ib) wherein $R_{2b}$ is H, $R_{3b}$ is Me, $R_{4b}$ is Cl, $R_{5b}$ is heptyl and $R_{6b}$ is H;
a compound of Formula (Ib) wherein $R_{2b}$ is H, $R_{3b}$ is Me, $R_{4b}$ is Cl, $R_{5b}$ is propyl-Ph and $R_{6b}$ is H;
a compound of Formula (Ib) wherein $R_{2b}$ is H, $R_{3b}$ is Me, $R_{4b}$ is Cl, $R_{5b}$ is decyl and $R_{6b}$ is H;
a compound of Formula (Ib) wherein $R_{2b}$ is H, $R_{3b}$ is Me, $R_{4b}$ is Cl, $R_{5b}$ is hexyl and $R_{6b}$ is H;
a compound of Formula (Ib) wherein $R_{2b}$ is H, $R_{3b}$ is Me, $R_{4b}$ is Cl, $R_{5b}$ is ethyl-2-(1-Me)pyrrolidinyl and $R_{6b}$ is H;
a compound of Formula (Ib) wherein $R_{2b}$ is H, $R_{3b}$ is Me, $R_{4b}$ is Cl, $R_{5b}$ is ethyl-1-pyrrolidinyl and $R_{6b}$ is H;
a compound of Formula (Ib) wherein $R_{2b}$ is H, $R_{3b}$ is Me, $R_{4b}$ is Cl, $R_{5b}$ is propyl-4-morpholinyl and $R_{6b}$ is H;
a compound of Formula (Ib) wherein $R_{2b}$ is H, $R_{3b}$ is Me, $R_{4b}$ is Cl, $R_{5b}$ is ethyl-4-morpholinyl and $R_{6b}$ is H;
a compound of Formula (Ib) wherein $R_{2b}$ is H, $R_{3b}$ is Me, $R_{4b}$ is Cl, $R_{5b}$ is Ph and $R_{6b}$ is H;
a compound of Formula (Ib) wherein $R_{2b}$ is H, $R_{3b}$ is Me, $R_{4b}$ is Cl, $R_{5b}$ is propyl-OC(O)-2-piperidinyl and $R_{6b}$ is H;
a compound of Formula (Ib) wherein $R_{2b}$ is H, $R_{3b}$ is Me, $R_{4b}$ is Cl, $R_{5b}$ is t-butyl and $R_{6b}$ is H;
a compound of Formula (Ib) wherein $R_{2b}$ is H, $R_{3b}$ is Me, $R_{4b}$ is Cl, $R_{5b}$ is n-butyl and $R_{6b}$ is Me;
a compound of Formula (Ib) wherein $R_{2b}$ is H, $R_{3b}$ is Me, $R_{4b}$ is Cl, $R_{5b}$ is H and $R_{6b}$ is H;
a compound of Formula (Ib) wherein $R_{2b}$ is Me, $R_{3b}$ is Cl, $R_{4b}$ is H, $R_{5b}$ is H and $R_{6b}$ is H;
a compound of Formula (Ib) wherein $R_{2b}$ is ethyl, $R_{3b}$ is Me, $R_{4b}$ is Cl, $R_{5b}$ is H and $R_{6b}$ is H;
a compound of Formula (Ib) wherein $R_{2b}$ is Me, $R_{3b}$ is Cl, $R_{4b}$ is Me, $R_{5b}$ is H and $R_{6b}$ is H;
a compound of Formula (Ib) wherein $R_{2b}$ is Me, $R_{3b}$ is Cl, $R_{4b}$ is Cl, $R_{5b}$ is H and $R_{6b}$ is H; and,
a compound of Formula (Ib) wherein $R_{2b}$ is Me, $R_{3b}$ is Cl, $R_{4b}$ is F, $R_{5b}$ is H and $R_{6b}$ is H.

* * * * *